(12) United States Patent
Izz

(10) Patent No.: US 6,929,118 B1
(45) Date of Patent: Aug. 16, 2005

(54) PROPHYLACTIC WRAPPER

(75) Inventor: Nofel Izz, Brampton (CA)

(73) Assignee: Flip Easy Inc., Brampton (CA)

( * ) Notice: Subject to any disclaimer, the term of this patent is extended or adjusted under 35 U.S.C. 154(b) by 0 days.

(21) Appl. No.: 10/923,801

(22) Filed: Aug. 24, 2004

(51) Int. Cl.⁷ .............................................. B65D 85/14
(52) U.S. Cl. .................................................... 206/69
(58) Field of Search .......................... 206/69, 530, 534; 128/842, 844, 918; 604/347, 351, 352, 399

(56) References Cited

U.S. PATENT DOCUMENTS

| | | | |
|---|---|---|---|
| 3,136,417 A * | 6/1964 | Clinch | 206/69 |
| 4,875,491 A * | 10/1989 | Parrone | 206/69 |
| 4,987,905 A | 1/1991 | Broad, Jr. | |
| 5,437,286 A | 8/1995 | Stratton | |
| 5,551,612 A * | 9/1996 | Hochfeld | 206/69 |
| 5,651,374 A | 7/1997 | Wester | |
| 6,089,231 A * | 7/2000 | Thompson | 128/918 |
| 6,718,983 B1 * | 4/2004 | Suzuki | 128/844 |

* cited by examiner

*Primary Examiner*—Luan K. Bui
(74) *Attorney, Agent, or Firm*—Cahn & Samuels, LLP.

(57) ABSTRACT

A rolled condom is sealed in a package having top and bottom walls, with the closed end of the condom facing the top wall and the open end facing the bottom wall. A peel-off label covers a substantial portion of each of the top and bottom walls, with a connecting neck portion wrapped over one peripheral edge. Cuts are formed in each of the top and bottom walls in a radially directed "X" pattern from the center of each wall, directed at the center point of each edge, or at each corner. A notch is formed at the center point of each edge, or at the corners. Before use, the peel-off label covers all of the cuts, and is peeled away for use. The material of the package is a frangible plastics material which will break away as the condom is applied.

10 Claims, 5 Drawing Sheets

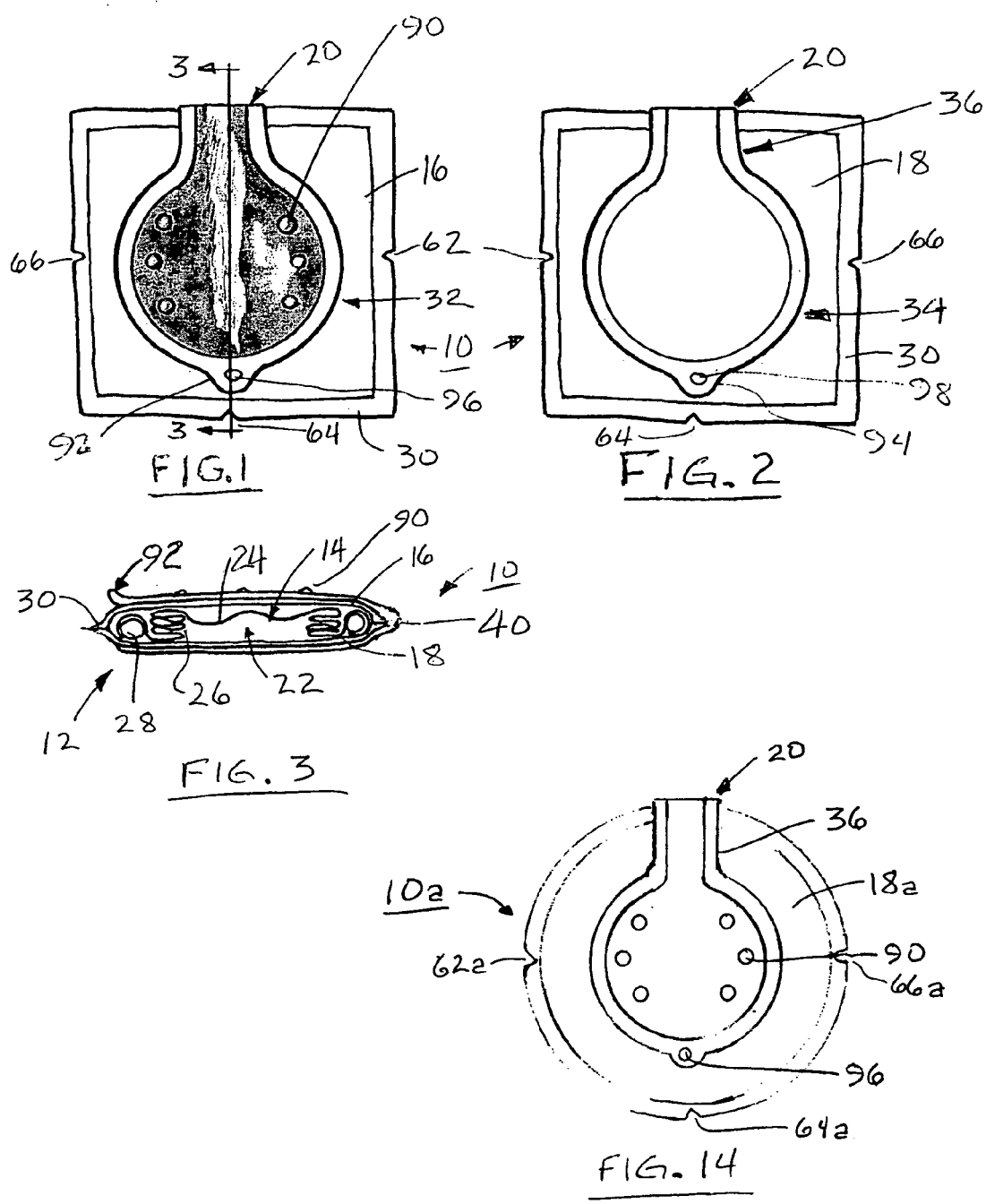

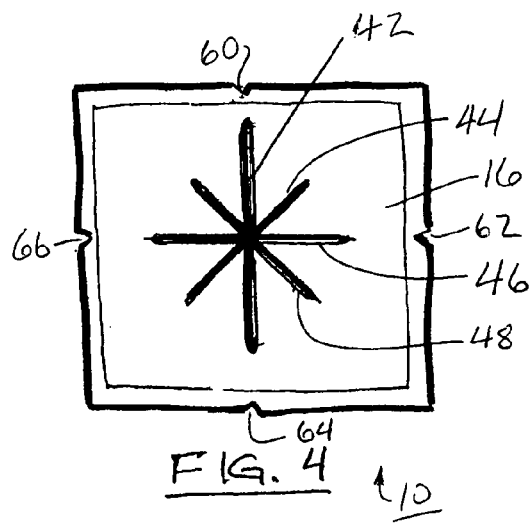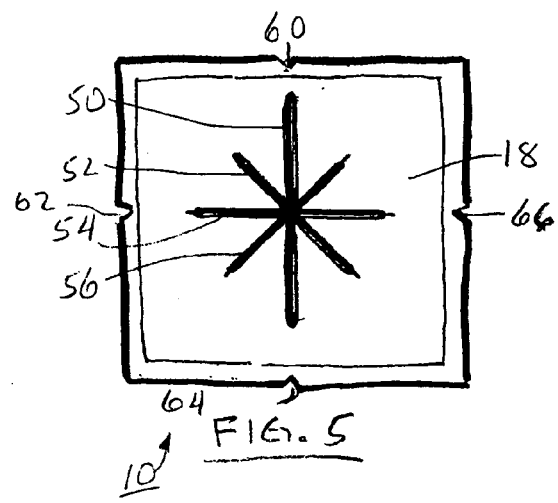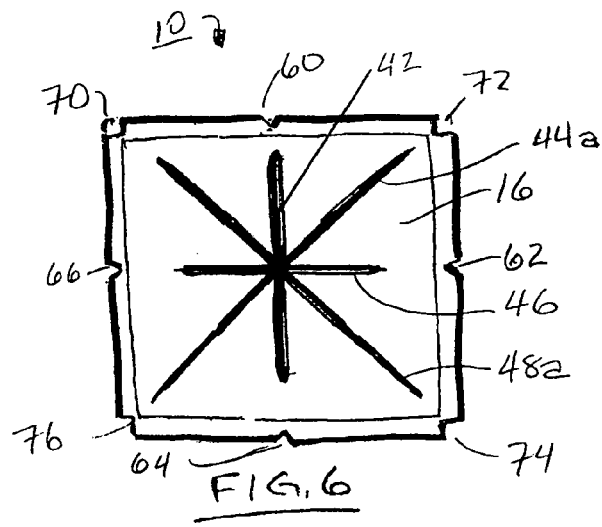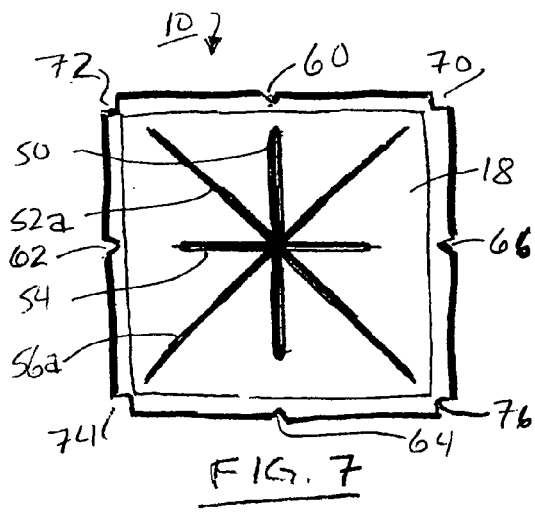

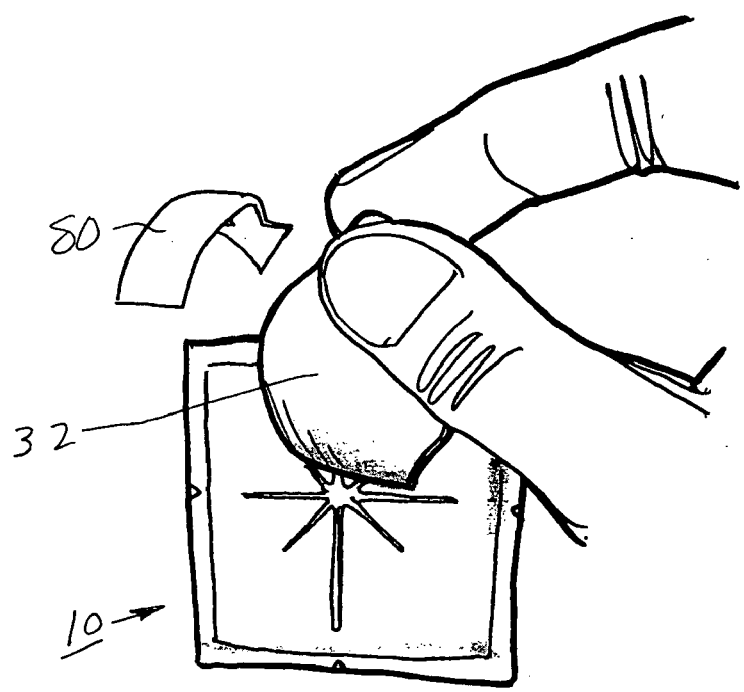
FIG. 8
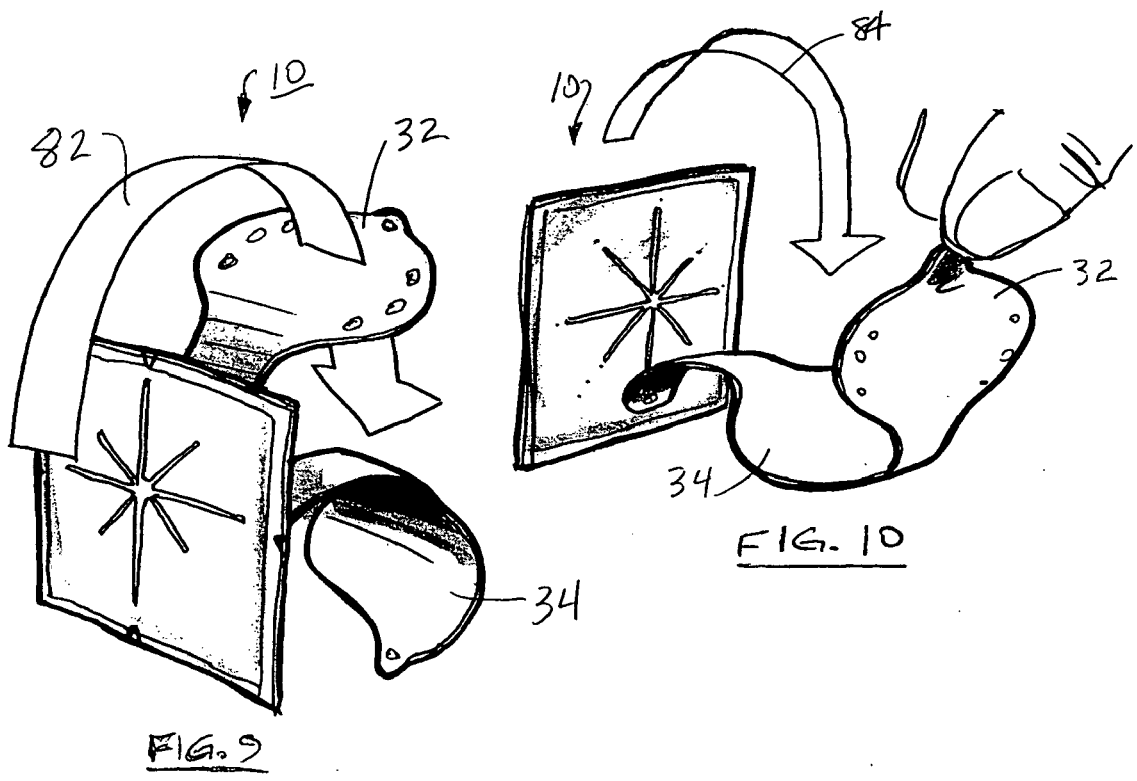
FIG. 9
FIG. 10

PROPHYLACTIC WRAPPER

FIELD OF THE INVENTION

This invention relates to packaged condoms, and particularly it relates to packages for condoms from which the condom may be removed using essentially a one-hand operation and placed directly over an erect penis. The package provides a sterile, moisture-proof package for a condom—which is typically pre-lubricated—and is one from which the condom does not need to be extracted. Rather, in use, the package essentially falls away from the condom as it is being put into place over an erect penis.

BACKGROUND OF THE INVENTION

The use of condoms is well-known. Their purposes are manifold, including particularly the prevention of unwanted pregnancy. However, in recent years, condoms have been more and more employed by persons whose sexual partner is not necessarily their married spouse. Nonetheless, there is a very active campaign against the spread of venereal disease or other sexually-transmitted diseases, among young people in particular, by promoting the use of condoms in all sexual encounters. This has led to the distribution of condoms from health and family planning centers located on many college and university campuses, and from Public Health Authorities and the like.

However, more recently, there has also developed a widespread of incidence of AIDS or HIV, particularly in the African continent, and now also Southeast Asia and the Indian subcontinent. Regrettably, in some instances, AIDS passes from person to person as a consequence of ingrown cultural beliefs. More particularly, however, it is also believed that the spread of AIDS, particularly in the African continent, comes as a consequence of a lack of condoms, and particularly ones which can be easily and intuitively applied to an erect penis by the male or his partner, without having to fumble and remove a condom from an envelope.

The same criterion has also led to the development of the condom package of the present invention when it applies to persons such as young married couples, or at least couples in love with one another, but whose amorous encounters beg the use of a condom for any of the purposes discussed above, particularly so as to avoid an unwanted pregnancy.

In such instances, it is well-known that the sexual act which will follow will be a more pleasant experience, as well as being safer, if the condom can be put into place quickly, and preferably with one hand.

To that end, therefore, the present invention provides. packages for condoms which can be easily opened so as to extract the condom therefrom, in many cases using one hand or at least only very temporarily requiring the use of two hands.

Moreover, it is an intent and purpose of the present invention to provide packaged condoms in packages which can be economically prepared so as to bring them to the market at a reasonably low cost. This is particularly important when it is considered that the supply of condoms to the African continent, and elsewhere, will be one of the major factors in preventing the spread of AIDS or HIV. Obviously, prevention of the spread of AIDS is much less expensive, in the long run, than providing drugs to combat the effects of AIDS on individuals suffering therefrom; so the supply of easily applied condoms at low cost becomes, in essence, a health issue having long-term, international, ramifications.

The present inventor has unexpectedly discovered that it is possible to supply a packaged condom using a frangible plastics material of the sort of packaging material presently used for ordinary condom envelopes, which require to be torn at one end so as to extract the condom therefrom. However, it is possible to apply a seal over a cut formed in such packaging material using a label having low tack adhesive for easy removal when desired, where the frangible plastics material of the package has been pre-cut and where notches have been located so as to face the ends of the cuts in order to induce failure and therefore tearing or breaking of the package, when appropriate. Moreover, the inventor herein has discovered a way in which tactile differentiation of the orientation of the still rolled condom within a package can be determined so as to ensure that the condom is correctly placed over an erect penis. This assures easy rolling of the flexible ring portion of the condom at the open end thereof, and it also ensures that if there is such as a spermicide included in the interior of the condom, or it is tipped or shaped in such a manner as to collect ejaculate, that these criteria are met and that the proper orientation of the condom over the erect penis is preserved.

Several other features which provided added value for young couples, in particular, can also be employed in condom packages in keeping with the present invention, such as making at least a portion of them luminous so that they may be found in relative darkness.

Nonetheless, the principal feature is to provide a properly sealed condom in a package which will break or tear in the appropriate circumstances and at the appropriate time, by simple removal of a label which covers cuts formed in the top and bottom walls of the condom package so that, upon application of force as the condom is being put into place over an erect penis, the package will tear or break so as to be easily discarded, while assuring that the placement of the condom is correct and is easily attended to.

DESCRIPTION OF THE PRIOR ART

Broad Jr., U.S. Pat. No. 4,987,905 teaches a contraceptive device having a condom where a rolled portion is positioned between a pair of sheets which are secured around the edges thereof to form a package for the condom. When the strips are pulled, the condom is unrolled, and the strips are such that they can be torn into two parts with the condom being pulled out of the package without premature unrolling.

Another condom holder is taught by Stratton, U.S. Pat. No. 5,437,286. Here, the condom holder has a condom carriage member that is U-shaped, with rupturable inner and outer packaging film members. The outer packaging surface is treated so as to identify and assure proper wear orientation of the packaged condom. Here, however, the U-shaped condom holder is laterally removable from the position condom, thereby providing what is, in essence, an additional packaging feature or element.

Wester, U.S. Pat. No. 5,651,374 teaches a package and applicable condom assembly where a circumferential tear line is provided around the open end of the condom, and there is at least one pull tab which is pulled laterally sideways to facilitate placement of the condom.

SUMMARY OF THE INVENTION

In accordance with one aspect of the present invention, there is provided a packaged condom which comprises, in combination, a rolled condom and a package therefor.

The rolled condom has an open end having a flexible ring portion, a closed end, and a rolled and folded tubular wall therebetween. The rolled condom has a greater diameter than height when the tubular wall is in its rolled and folded condition.

The package comprises a top wall and a bottom wall, each having a rectangular configuration. The walls are sealed one to the other around their respective peripheries, so as to enclose the rolled condom therein. The closed end of the rolled condom faces the top wall of the package, and the open end of the condom faces the bottom wall of the package.

A peel-off label is provided, and it covers a substantial portion of each of the top and bottom walls. Thus, a substantial portion of the area of the top and bottom walls is understood to mean not the entire area, but most of it; and at least that portion of the top and bottom walls where cuts have been made during manufacture of the packaging in keeping with the present invention. The peel-off label comprises a top label portion and a bottom label portion, with a connecting neck portion therebetween which is wrapped over one peripheral edge of the top and bottom walls.

At least two cuts are formed in each of the top and bottom walls, and are arranged in a radially directed "X" pattern from the center of each of the top and bottom walls. The cuts are directed at the peripheral edges of the top and bottom walls in directions which are substantially 90° apart.

A plurality of notches is formed in the peripheral edges of the sealed together top and bottom walls, in locations at which the at least two cuts are radially directed.

In any event, before use, the peel-off label covers all of the cuts in each of the top and bottom walls.

Typically, the condom package has a rectangular configuration, but the present invention contemplates that the package may also be round or oval.

However, when the package has a rectangular configuration, the at least two cuts are directed at each peripheral edge of the top and bottom walls at the center point thereof, or at each corner of each of the top and bottom walls.

Where the package has a rectangular configuration, there is a notch formed either at the center point of each peripheral edge, if the cuts extend radially towards the center points of each of the peripheral edges; or at the corners of the top and bottom if the cuts extend radially towards those corners.

Typically, there are four cuts in each of the top and bottom walls, and they are arranged substantially 45° apart, in a star pattern which is radially directed from the center of each of the top and bottom walls.

In a preferred embodiment, the two cuts which extend radially towards the center points of each of the peripheral edges of the top and bottom walls are longer than the two cuts which extend radially towards the corners of the top and bottom walls.

In this case, notches are formed at the center points of each of the peripheral edges of the top and bottom walls.

The material of each of the top and bottom walls of the package is a frangible plastics material.

The peel-off label is held in place by a low tack adhesive.

Typically, the top label portion of the peel-off label is embossed so as to provide tactile recognition thereof.

Also, a tab portion is provided on at least the top label portion of the peel-off label in a position opposite to the connecting neck portion.

Typically, at least the top portion on the top label portion of the peel-off label is embossed so as to provide tactile recognition of that tab portion.

At the least the top label portion of the peel-off label may be treated so as to be luminous.

BRIEF DESCRIPTION OF THE DRAWINGS

The novel features which are believed to be characteristic of the present invention, as to its structure, organization, use and method of operation, together with further objectives and advantages thereof, will be better understood from the following drawings in which a presently preferred embodiment of the invention will now be illustrated by way of example. It is expressly understood, however, that the drawings are for the purpose of illustration and description only and are not intended as a definition of the limits of the invention. Embodiments of this invention will now be described by way of example in association with the accompanying drawings in which:

FIG. 1 is a top view of a condom package, with peel-off label in place;

FIG. 2 is a bottom view of a condom packaging in keeping with the present invention, also with the peel-off label in place;

FIG. 3 is an elevation taken along arrows 3—3 in FIG. 1;

FIG. 4 is a top view of a preferred embodiment of the present invention, with the peel-off label having been removed;

FIG. 5 is a bottom view of the preferred embodiment of the present invention, also with the peel-off label removed;

FIG. 6 is a top view of an alternative embodiment of the present invention, with the peel-off label removed;

FIG. 7 is a bottom view of the alternative embodiment of the present invention, also with the peel-off label having been removed;

FIG. 8 illustrates the first step in removing the peel-off label from a package in keeping with the present invention;

FIG. 9 continues the action of FIG. 8;

FIG. 10 continues the action of FIG. 9, showing the label being totally removed from the package;

FIG. 14 shows an alternative configuration of the package.

DETAILED DESCRIPTION OF THE PREFERRED EMBODIMENTS

Figure 11:
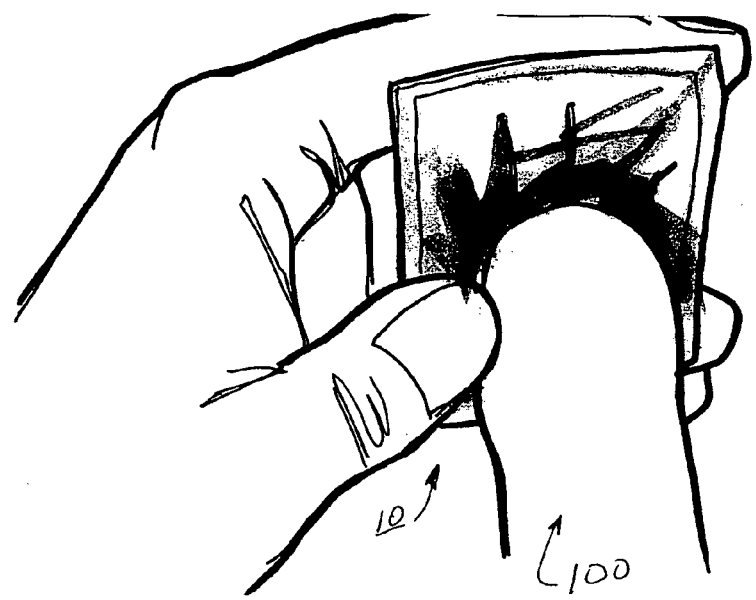
FIG. 11 demonstrates the first operative step in placing the packaged condom over an erect penis.

The novel features which are believed to be characteristic of the present invention, as to its structure, organization, use and method of operation, together with further objectives and advantages thereof, will be better understood from the following discussion.

Turning first to FIGS. 1, 2, and 3, the combination of a condom and a package therefor is shown at 10. That combination comprises a package shown generally at 12, and a rolled condom shown generally at 14.

The package comprises a top wall 16 and a bottom wall 18, and a peel-off label shown generally at 20.

The rolled condom 14 has an open end 22, a closed end 24, and a rolled and folded tubular wall 26. The tubular wall 26 terminates in a flexible ring portion 28. The precise details of the condom 14 are not relevant to the present invention insofar as whether or not the condom is pre-lubricated or not, or whether it has a tip for collection of ejaculate, etc.

Nonetheless, it will be understood from FIG. 3, as well as from FIGS. 1 and 2, that the rolled condom 14 has a greater diameter than its height when the tubular wall 26 is in its rolled and folded condition, as shown in FIG. 3.

It will be seen that the top and bottom walls 16 and 18 each have a rectangular configuration. Typically, that configuration is square.

It will be understood from FIG. 3, as well as from FIGS. 1 and 2, that the top wall 16 and the bottom wall 18 are sealed one to the other around their respective peripheries, as at 30.

It will also be seen, in particular from FIG. 3, that the closed end 24 of the rolled condom 14 faces the top wall 16, while the open end 22 of the rolled condom 14 faces the bottom wall 18. Obviously, the orientation of the condom within the package will become important at the time when the condom is to be applied over an erect penis.

The peel-off label 20 covers a substantial portion of each of the top and bottom side walls 16, 18 as is seen in FIGS. 1 and 2.

In any event, the peel-off label 20 completely covers a plurality of cuts formed in each of the top and bottom walls 16, 18, so as to ensure sterile and hermetic sealing of the packaged condom 14. The peel-off label 20 comprises a top label portion 32 and a bottom label portion 34. There is a connecting neck portion 36 between the top and bottom label portion 32, 34, and it is wrapped over one peripheral edge of the sealed-together top and bottom walls 16, 18, as shown at 40 in FIG. 3.

In a preferred embodiment of the present invention, there are four cuts in each of the top and bottom walls 16 and 18, as shown at 42, 44, 46, 48 in FIG. 4, being the four cuts in the top wall 16; and at 50, 52, 54, 56, being the four cuts in the bottom wall 18, as shown in FIG. 5.

An alternative embodiment is shown in FIGS. 6 and 7, where cuts 44a and 48a in the top wall 16, and 52a and 56a in the bottom wall 18, are much longer than in the preferred embodiment shown in FIGS. 4 and 5.

It will also be seen in FIGS. 4 and 5 that there are four notches formed around the periphery of the package 10, at 60, 62, 64, and 66. Each is at the center point of the respective peripheral edge of the sealed-together top and bottom walls 16, 18.

In the alternative embodiment, notches are formed in the corners at 70, 72, 74, and 76, respectively.

It will be seen in FIGS. 4 and 5 that the cuts 42 and 46 are longer than the cuts 44 and 48, in the top wall 16; and likewise the cuts 50 and 54 are longer than the cuts 52 and 56, in the bottom wall 18. Thus, as will be described hereafter, a fault area will be found between the respective ends of the cuts 42 and 46, and 50 and 54, and the notches 60, 62, 64, 66. It will be recalled that the material of the package, particularly that of the top and bottom walls 16, 18, is a frangible plastics material, so that as will be discussed in greater detail hereafter, a fault or failure will occur at one of those fault areas so that the top and bottom walls 16 and 18 will tear or break away in keeping with the present invention.

Having regard to cuts 42 and 46, for example, or cuts 44 and 48, as seen in FIG. 4, and the same or similar cuts as shown in FIGS. 5, 6, and 7, it will be seen that there can be at least two cuts 42, 46 or 44a, 48a, which are arranged in a radially directed "X" pattern, emanating from the center of each of the top and bottom walls 16, 18. Each of the cuts is directed to the peripheral edges of the top and bottom walls 16, 18 at the center point thereof, as seen in cuts 42, 46, 50, and 54 in FIGS. 4 and 5; or at the corners as seen at cuts 44a, 48a, 52a, and 56a in FIGS. 6 and 7.

The purpose for the longer cuts is, as noted above, to induce a failure of the material of the top and bottom walls 16, 18, at an appropriate time as the condom 14 is being applied over an erect penis.

Turning now to FIGS. 8 to 13, the application of a condom to an erect penis from the package of the present invention will now be understood.

Figure 12:
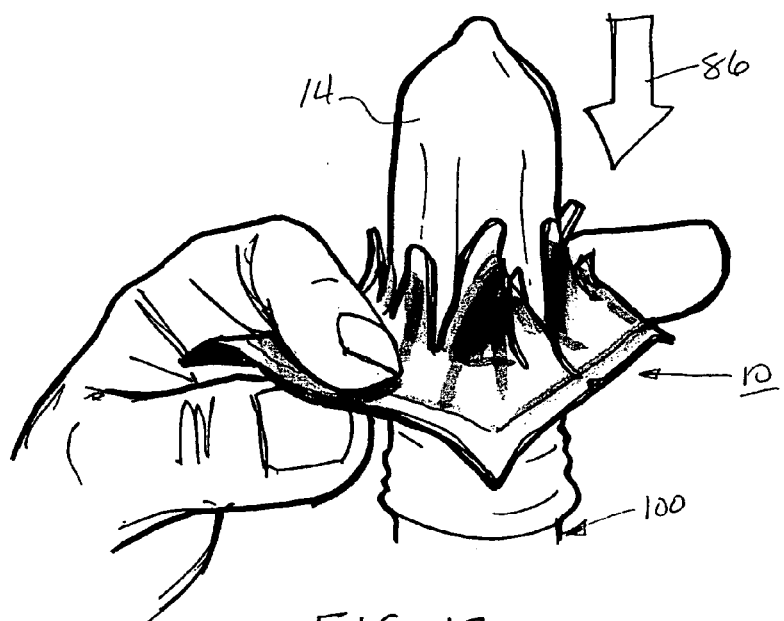
FIG. 12 shows the continuation of the step from FIG. 11.

First, the peel-off label 20 is removed from the package 10, by lifting the top label portion 32 and peeling it away as shown by arrow 80. The action is continued as shown in FIG. 9 at arrow 82, and is concluded as shown in FIG. 10 at arrow 84. By this time, the package is devoid of its peel-off label, which previously has provided appropriate sterile and hermetic sealing for the package. Now, as seen in FIG. 11, the package is ready for application of the condom over an erect penis 100. The process continues as shown in FIG. 12, whereby the condom 14 is unrolled as shown at arrow 86. By then, it will be understood that the material of the top wall 16 and bottom wall 18 is breaking apart, and all of the cuts in the top and bottom walls 16, 18 are extending as can be clearly understood from FIG. 12.

Figure 13:
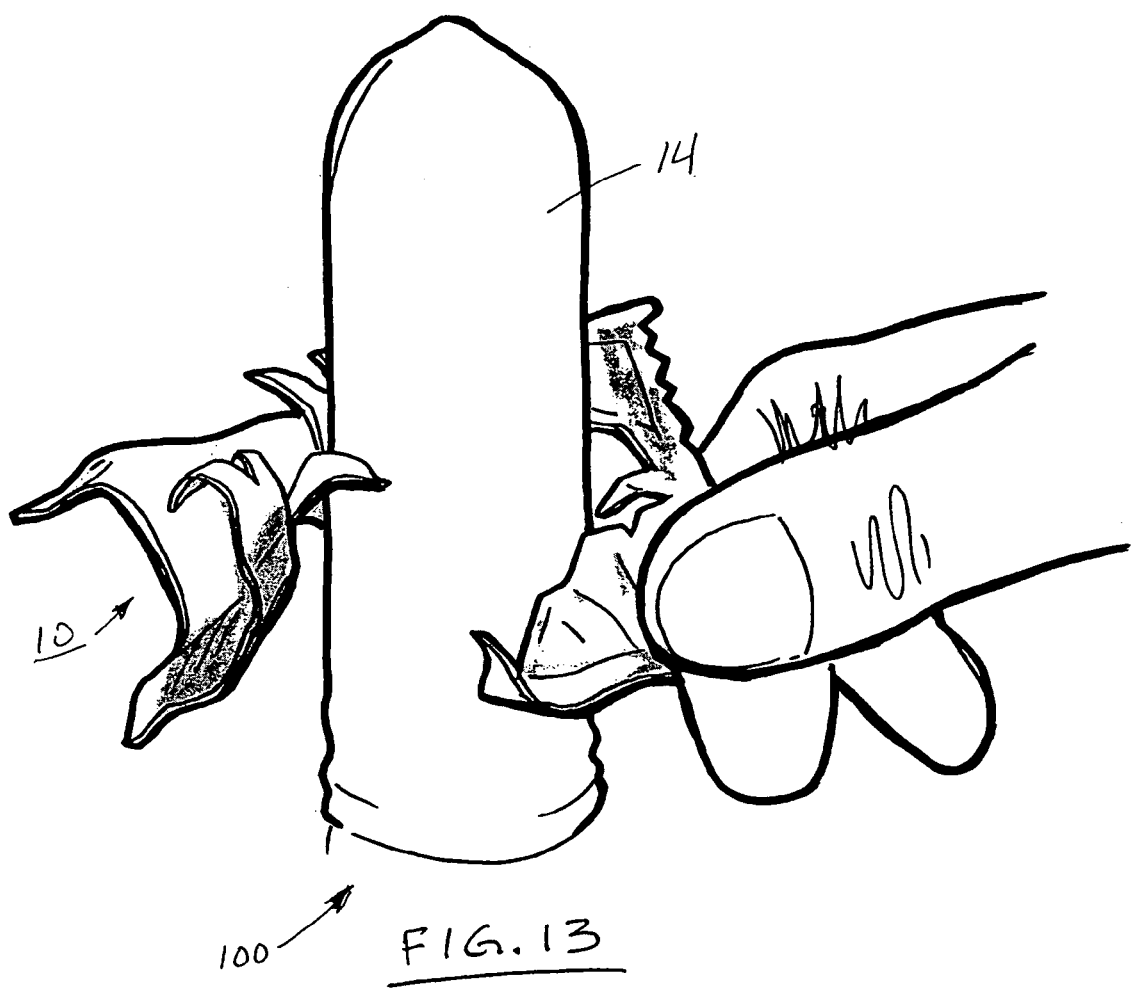
FIG. 13 illustrates the condom in place over an erect penis, and the package from which it has been removed being discarded.

Finally, a fault will occur as seen in FIG. 13 at one of the notches; in this case, and in the preferred embodiment, it would be one of notches 60, 62, 64, 66.

It will, of course, be understood from FIGS. 4 to 7 that the cuts, when there are four of them, are arranged at substantially 45° one from another, so as to be in a star pattern radially directed from the center of each of the top and and bottom walls 16, 18. Thus, as noted above, two of the cuts are longer than the other two; and they may be cuts 42, 46, 50, 54 as shown in FIGS. 4 and 5; or cuts 44a, 48a, 52a, 56a, as shown in FIGS. 6 and 7. In any event, as is now clearly understood, a failure or fault area is developed at the end of the cuts between one or another of those ends and the respective notch which it faces.

So as to ensure that the orientation of the package is correct, typically the top label portion 32 of the peel-off label 20 is embossed as at 90. This will permit tactile recognition of the top portion of the package 10 as opposed to the bottom portion, so that even in the dark proper orientation of the package, and therefore proper orientation of the rolled condom 14 over an erect penis 100 will be achieved.

Also, so as to permit easy removal of the peel-off label 20, tab portions may be formed at least on the top label portion 32, as shown at 92, in a position which is opposite to the connecting neck portion 36. That tab portion 92 may be embossed as at 96.

Similar tab portions 94, with an embossment 98, may be formed as well in the bottom label portion 34 of the peel-off label 20, as seen in FIG. 2.

The shaded area of the top label portion 32, as seen in FIG. 1, may also be treated so as to be luminous. It will therefore permit the package 10 to be found in the dark.

Finally, turning to FIG. 14, it will be understood that the package may be round or oval, and exhibit the same characteristics otherwise. Thus, package 10a has a round configuration, with the same peel-off label 20. Notches 62a, 64a, 66a are formed in the peripheral edges of the package. It will be understood that the same configuration of cuts in the top wall 18a, and the bottom wall, will be found as previously described, and will function in the same manner.

There has been described a package for a condom which permits the condom to be supplied to its ultimate user in a sterile and hermetic condition, but which permits easy removal of the package away from the condom—as opposed to removal of the condom away from the package. As described, the condom is first placed over an erect penis while still in the package, and the simple expedient of beginning to unroll the condom down the erect penis will ensure that the frangible material of the top and bottom walls of the package will fail at one of several induced failure regions, so that the package essentially breaks away and can be then easily discarded.

A preferred and alternative embodiments have been illustrated and described. However, it will be clear to those skilled in the art that other embodiments may also be developed that do not part from the spirit and scope of the appended claims.

It will be understood that use of the word "substantial" or "substantially" means, in general, not entirely but mostly, on a relatively major portion as opposed to a minor portion of the area of a surface.

Throughout this specification and the claims which follow, unless the context requires otherwise, the word "comprise", and variations such as "comprises" or "comprising", will be understood to imply the inclusion of a stated integer or step or group of integers or steps but not to the exclusion of any other integer or step or group of integers or steps.

What is claimed is:

1. A packaged condom comprising, in combination, a rolled condom and a package therefor; wherein said rolled condom has an open end having a flexible ring portion, a closed end, and a rolled and folded tubular wall therebetween, said rolled condom having a greater diameter than height when said tubular wall is in said rolled and folded condition;

said package comprising a top wall and a bottom wall, and being sealed one to the other around their respective peripheries so as to enclose said rolled condom therein, with said closed end of said rolled condom facing said top wall of said package and said open end of said condom facing said bottom wall of said package; and a peel-off label covering a substantial portion of each of said top and bottom walls, and comprising a top label portion and a bottom label portion with a connecting neck portion therebetween which is wrapped over one peripheral edge of said top and bottom walls;

at least two cuts in each of said top and bottom walls being arranged in a radially directed "X" pattern from the center of each of said top and bottom walls, and being directed at the peripheral edges of said top and bottom walls in directions which are substantially 90° apart;

a plurality of notches formed in the edges of said sealed together top and bottom walls in locations at which at least said two cuts are radially directed; and wherein, before use, said peel-off label covers all of the cuts in each of said top and bottom walls.

2. The condom package of claim 1, wherein said package has a rectangular configuration;

wherein said at least two cuts are directed at each peripheral edge of the top and bottom walls at the center point thereof, or at each corner of each of said top and bottom walls; and wherein a notch is formed either at the center point of each peripheral edge if the cuts extend radially thereat, or at the corners of the top and bottom walls if the cuts extend radially thereat.

3. The condom package of claim 1, wherein said package has a configuration chosen from the group consisting of round and oval.

4. The condom package of claim 2, wherein there are four cuts in each of said top and bottom walls arranged substantially 45° apart, and in a star pattern radially directed from the center of each of said top and bottom walls;

wherein, the two cuts which extend radially towards the center points of each peripheral edge of said top and bottom walls are longer than the two cuts which extend radially towards the corners of said top and bottom walls; and wherein, notches are formed at the center points of each of said peripheral edges of said top and bottom walls.

5. The condom package of claim 1, wherein the material of each of said top and bottom walls of said package is a frangible plastics material.

6. The condom package of claim 1, wherein said peel-off label is held in place by a low tack adhesive.

7. The condom package of claim 1, wherein the top label portion of said peel-off label is embossed so as to provide tactile recognition thereof.

8. The condom package of claim 1, wherein a tab portion is provided in at least said top label portion of said peel-off label, in a position opposite to said connecting neck portion.

9. The condom package of claim 6 wherein at least said tab portion on said top label portion of said peel-off label is embossed so as to provide tactile recognition thereof.

10. The condom package of claim 1, wherein at least said top label portion of said peel-off label is treated so as to be luminous.

* * * * *